(12) United States Patent
Aali et al.

(10) Patent No.: US 8,334,423 B2
(45) Date of Patent: *Dec. 18, 2012

(54) SYSTEMS AND METHODS FOR WOUND PROTECTION AND EXUDATE MANAGEMENT

(75) Inventors: Adel Aali, Irvine, CA (US); Raymond Barbuto, Dagsboro, DE (US)

(73) Assignee: Aalnex, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/305,569

(22) Filed: Nov. 28, 2011

(65) Prior Publication Data

US 2012/0191026 A1    Jul. 26, 2012

Related U.S. Application Data

(63) Continuation of application No. 12/416,826, filed on Apr. 1, 2009, now Pat. No. 8,067,662.

(51) Int. Cl.
*A61F 13/00* (2006.01)

(52) U.S. Cl. .......................... 602/43; 604/304

(58) Field of Classification Search .............. 602/41–58; 604/289, 290, 304–308, 540; 128/888–889
See application file for complete search history.

(56) References Cited

U.S. PATENT DOCUMENTS

| | | | | |
|---|---|---|---|---|
| 4,972,829 A | * | 11/1990 | Knerr | 602/52 |
| 5,060,662 A | * | 10/1991 | Farnswoth, III | 128/888 |
| 2002/0026133 A1 | * | 2/2002 | Augustine et al. | 602/2 |

* cited by examiner

*Primary Examiner* — Loan Thanh
*Assistant Examiner* — Tarla Patel
(74) *Attorney, Agent, or Firm* — Jones Day; Nicola A. Pisano; Jaime D. Choi

(57) ABSTRACT

The present invention provides systems and methods for protecting a wound and managing exudate released from the wound comprising a dressing having a support cushion for surrounding the wound and periwound region; a wicking strip for application in the periwound region between the support cushion and the wound; and a reservoir for application over the wicking strip, the wicking strip configured to transfer exudate from the wound to the reservoir, where the exudate is sequestered. Various alternative embodiments are described in which the wicking strip may be custom-fit to approximate an irregular wound margin, to apply a preferred pressure gradient to the periwound regions, to periodically apply fluids to the wound bed or to apply negative pressure wound therapy. Methods of applying the dressing also are provided.

20 Claims, 7 Drawing Sheets

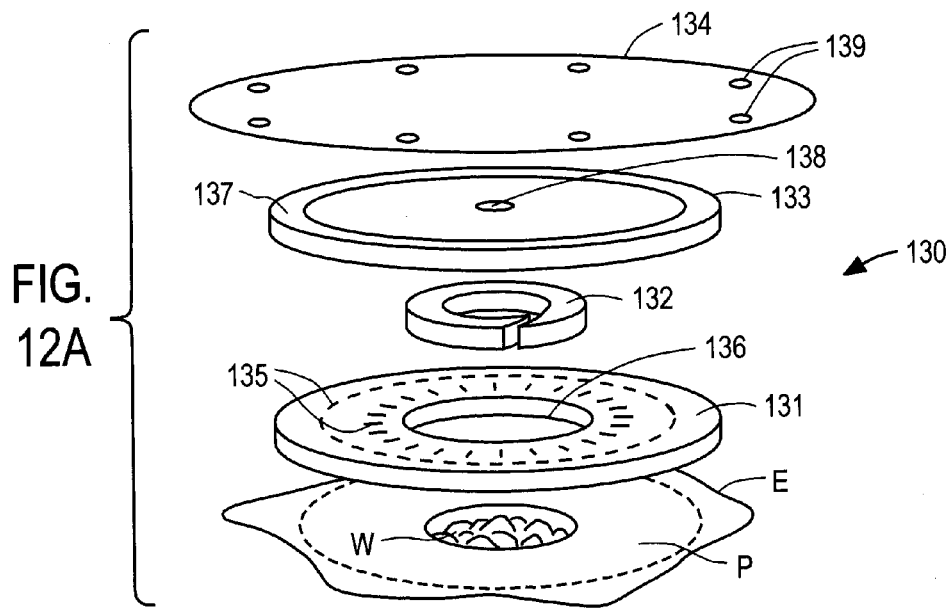
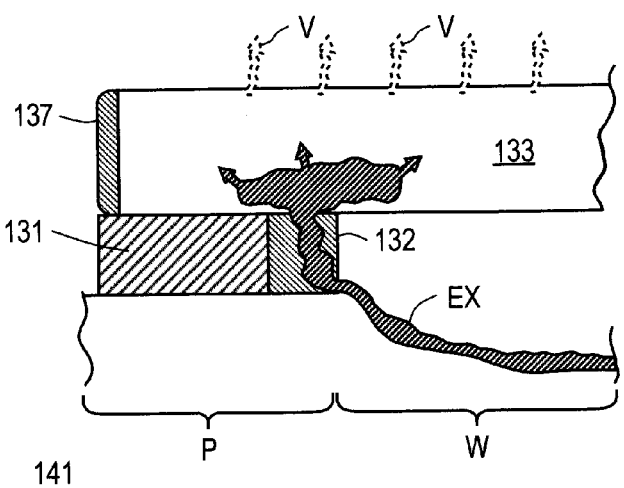
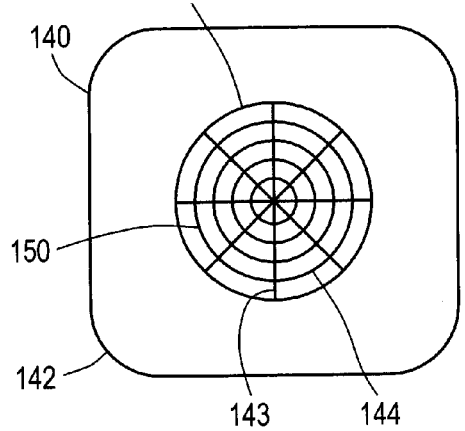
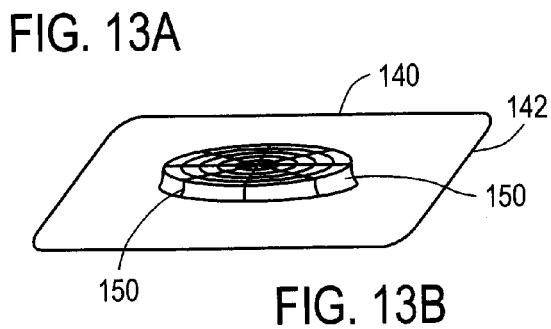

SYSTEMS AND METHODS FOR WOUND PROTECTION AND EXUDATE MANAGEMENT

I. CROSS-REFERENCE TO RELATED APPLICATIONS

This application is a continuation under 35 U.S.C. §120 of U.S. patent application Ser. No. 12/416,826, filed Apr. 1, 2009 now U.S. Pat. No. 8,067,662 and entitled "Systems and Methods for Wound Protection and Exudate Management," the entire contents of which are incorporated by reference herein.

II. FIELD OF THE INVENTION

This application generally relates to systems and methods for promoting the healing of wounds, and particularly to systems and methods for promoting the healing of wounds that generate exudate.

III. BACKGROUND OF THE INVENTION

Wounds occur when the integrity of tissue is compromised, affecting one or more layers of the epidermis or underlying tissue. Acute wounds may be caused by an initiating event, such as a accident-related injury, surgical procedure or by operation of an infectious disease, and generally take the form of punctures, abrasions, cuts, lacerations, or burns. Chronic wounds are wounds that generally do not heal within three months, due to one or more of: ischemia of the vessels supplying the tissue, venous hypertension or compromise of the immune response, such as observed, for example, with venous ulcers, diabetic ulcers and pressure ulcers. Depending on etiology, such as diabetes, venous insufficiency, or cardiovascular failures, acute wounds may become recalcitrant and even chronic.

The introduction of bacteria from external sources into the wound typically causes inflammation that activates the patient's immune response, in turn causing white blood cells, including neutrophil granulocytes, to migrate towards the source of inflammation. While they fight pathogens, such neutrophils also release inflammatory cytokines and enzymes that damage cells. In particular, the neutrophils produce an enzyme called myeloperoxidase that in turn is metabolized to produce reactive oxygen species that kill bacteria. Collaterally, such enzymes and reactive oxygen species damage cells in the margin surrounding the wound, referred to as the "periwound," thereby preventing cell proliferation and wound closure by damaging DNA, lipids, proteins, the extracellular matrix and cytokines that facilitate healing. Because neutrophils remain in chronic wounds for longer than in acute wounds, they contribute to higher levels of inflammation. Moreover, the persisting inflammatory phase in chronic wounds contributes to exudate (fluid that flows from the wound) with high concentrations of matrix metalloproteases (MMPs). Excess MMPs results in degradation of extracellular matrix protein. In addition to damaging the wound, exudate damages the periwound tissue exposed to it as well. In particular, exudate that flows out of the wound and onto periwound region may damage the fragile skin, which is already compromised due to the patients underlying etiology, such as diabetes. Such damage may degrade the periwound skin and cause its breakdown and turn it into a wound. Thus, exudate flow onto the periwound region will cause many complications, including, the potential for increasing the size of the wound and prolonging its healing. Such damage to the skin in the periwound region (periwound skin) makes it more susceptible to tearing and resultant intense pain as dressings or devices adhered to them are removed. Other complications include infection of the periwound region and intense itching.

Patients suffering from chronic wounds frequently report experiencing severe and persistent pain associated with such wounds, which may arise from necrosis of and/or nerve damage of the skin and underlying tissue. Treatment for such pain often consists of low dose analgesics, while topical antibiotics and/or debridement, which seeks to remove necrotic tissue from the wound, may be used to control the bacterial load at the wound site.

Conventional wound treatment also typically involves covering the wound with a dressing to prevent further contamination and infection, to retain moisture, and to absorb exudate. While exudate contains biochemical compounds that benefit wound healing as noted above, its excessive amount in wound or its presence in the periwound region facilitates degradation of tissue, and the exudate additionally serves as a growth medium for bacteria. The consistency of exudate varies, depending on the type of wound and the stage of healing. For example, exudate may be watery, extremely viscous, or somewhere in between. Moreover, the sizes of wounds can vary greatly, as can their care.

Although a wide variety of dressings have been developed, few previously-known wound treatment systems properly manage exudate, e.g., removing a sufficient amount of exudate from the wound site, while protecting the periwound region from damaging contact with the exudate. Moreover, conventional systems typically do not address the pain created by the wound treatment system, particularly where the wound treatment system continuously contacts the wound. For example, gauze, which is applied directly onto a wound, is capable of absorbing only a limited amount of exudate, and readily transports excess exudate onto the periwound region, causing maceration and damage. Moreover, the gauze typically is in direct contact with the wound and adheres to it, so that normal motion of the patient results in rubbing, itching and discomfort. In addition, removal of the gauze at periodic intervals is painful and frequently disrupts any healing that may have occurred.

Some previously-known approaches to wound treatment attempt to reduce adhesion between the wound and the dressing by applying additional substances. For example, the wound and dressing may be soaked in saline water to loosen adherence and/or soften any scabs that formed, thus facilitating removal of the dressing. Or, for example, antibiotic ointments such as polymyxin B sulfate or bacitracin can be applied to reduce sticking. However, such methods are not always satisfactory because soaking a particular wound in water or applying ointments may not be practicable or recommended.

Some previously-known dressings are promoted as being "non-stick" or "non-adherent," such as TELFA™ and XEROFORM™, and other brands that may be composed of materials such as hydrocolloids, alginates, and hydrofilms. Regardless of the level of adherence of such dressings to the wound, continuous contact between the dressing and wound disturbs the fragile wound matrix, and may undermine the growth of blood vessels and epithelial cells in the wound bed. Such disturbance often occurs when the dressing is removed, or simply as a result of the contact between the bandaged area and the patient's environment. Pain is often concomitant with such disturbances. In addition, previously-known "non-stick" dressings usually do not absorb sufficient amounts of exudate, and thus require frequent monitoring and changing.

These drawbacks add to the cost of use and limit the applicability of such previously-known wound treatment systems.

Previously-known dressings commonly have only a limited ability to manage wound exudate. As noted above, prolonged exposure of otherwise healthy skin to exudate may cause degradation of the periwound region. The moisture of the exudate may cause maceration, which is a softening of the skin that compromises its integrity and makes the skin in the periwound region vulnerable to physical insult and infection.

Some previously-known dressings attempt to manage exudate to address the foregoing issues, but provide either limited benefit and/or at a much higher perceived cost. For example, a foam dressing such as ALLEVYN® (marketed by Smith & Nephew, Largo, Fla., USA) is designed to absorb large amounts of exudate. However, use of this product is restricted to highly exuding wounds, because its highly absorptive properties can result in desiccation of wounds that are not highly exuding, thereby impeding healing. In addition, because foam used in that product cannot be conformed to the size and shape of the wound, the dressing typically overlaps with the periwound region. Consequently, exudate absorbed by the foam is transported throughout the foam and onto the periwound region, where prolonged exposure leads to maceration and degradation of the periwound region. Other previously-known dressings, such as ACQUACEL® hydrofiber dressing (available from ConvaTec, Inc., Princeton, N.J., USA) contact the wound bed, and are intended to absorb exudate and transfer and sequester the exudate in a layer disposed atop the wound. This and similar previously-known dressings do not entirely contain or absorb exudate. Moreover, like foam and other previously-known dressings, hydrofiber dressings essentially plug the wound surface, and create an osmotic environment in which the fluidic osmotic pressure within the wound bed approximates that of the surrounding tissue. Consequently, exudate is not sufficiently drawn from the wound, and its buildup in the wound may adversely affect the wound and periwound region. Furthermore, ALLEVYN®, ACQUACEL®, and similar previously-known dressings do not provide an adequate moisture vapor transfer rate (MVTR) away from the wound environment, thus creating the potential for an over-hydrated environment that hinders wound healing.

Other previously-known wound treatment systems, such as the V.A.C.® system, available from Kinetic Concepts, Inc. (San Antonio, Tex., USA), employ a mechanically operated contact-based dressing that continuously vacuums exudate from the wound bed. It and other dressings incorporating the concept of Negative Pressure Wound Therapy have proven particularly useful in healing large wounds, such as surgical wounds. However, such systems are costly, difficult to apply and time consuming. In addition, because such systems require insertion of a sponge (for the V.A.C.® system) or gauze (as commercialized by other wound care companies) directly into the wound bed, they likely cause considerable pain and discomfort for the patient, and may not be appropriate for many types of wounds.

Several previously-known dressings also have been developed that are promoted as "non-contact" dressings, which seek to prevent adhesion of the wound tissue to dressing, or to facilitate certain treatments that by their nature cannot contact the wound, e.g., thermal therapy. Such dressings are commonly formed as an inverted cup or a raised bandage that covers the wound without contacting it. Such previously-known dressings, however, also have failed to adequately heal wounds and protect the periwound region. Such non-contact dressings are provided in pre-formed shapes and sizes, and have limited deformability, thus limiting their ability to prevent exposure of the periwound skin to exudate. Additionally, the limited deformability of such previously-known dressings makes application of such dressings difficult or impossible to wounds on small surfaces or in areas with complex topology, such as the ankle or foot. Previously-known non-contact dressings also do not allow the pressure applied to the periwound region to be readily managed, and may result in the formation of pressure rings around the wound, thereby inducing ischemia in the wound and surrounding tissue. Finally, such previously-known dressings do not provide any mechanism to stimulate the flow of exudate, nor do they sequester exudate away from the wound in any appreciable volume. Such previously-known dressings also trap humidity over the wound and periwound region, leading to maceration, periwound degradation and impeded healing.

IV. SUMMARY OF THE INVENTION

The present invention provides systems and methods for treatment of wounds by managing exudate and cushioning wounds from external pressure sources. The dressing of the present invention may be used for a wide range of chronic wounds, including venous ulcers, diabetic foots ulcers, pressure ulcers, and arterial ulcers. In addition, dressings constructed in accordance with the present invention may be advantageously used for surgical wounds to protect the incision site, particularly for surgical areas where skin is most vulnerable, such as split-thickness graft sites and cosmetic surgeries.

Dressings constructed in accordance with the present invention also may advantageously used to treat acute wounds and to protect the wound from further trauma, such as occurs in industrial accidents and in the battle field settings. In particular, dressings in accordance with the present invention may be applied to reduce contact pressure on the wound bed. In a battlefield setting, for example, this aspect of the invention may be particularly valuable, since a bandaged wound may still have debris or shrapnel in it, and the dressing can be applied to prevent such contaminants from being pushed further into the wound during evacuation of the wounded subject.

In accordance with one aspect of the present invention, a system is provided for managing exudate released from a wound that is surrounded by a periwound region, the system including: a support cushion that surrounds the wound and the periwound region; a wicking strip configured to be applied in the periwound region between the support cushion and the margin of the wound; and a reservoir that is disposed over the wicking strip to absorb and sequester exudate from the wicking strip. The wicking strip may include a substantially hydrophobic film on the surface that contacts the periwound region, so that exudate is absorbed through a lateral surface of the wicking strip exposed to the wound bed, but exudate entering the wicking strip does not contact or cause maceration of the periwound tissue located beneath the hydrophobic film. Preferably, the hydrophobic layer may also serve as an adhesive that adheres the wicking strip to the periwound tissue at the margin of the wound.

In some embodiments, the support cushion includes a high-profile portion configured to accommodate the reservoir; and a low-profile portion configured to suspend the reservoir over the wound. The high-profile and low-profile portions of the support cushion may be hydrophobic; the wicking strip and the reservoir may be hydrophilic; the high-profile portion may inhibit lateral flow of exudate out of the reservoir; and the low-profile portion may inhibit lateral flow of exudate out of the wicking strip. In some embodiments, the support cushion also may include a plurality of slits to enhance conformability of the cushion to complex patient topology, and to allow the transfer of moisture vapor from the skin on which the support cushion rests.

Some embodiments further may include a cover secured to the reservoir; and a biocompatible adhesive for securing the cover to the support cushion, so that the adhesive urges the reservoir into engagement with the wicking strip. The wicking strip may have a length and a height, such that the height varies along the length to modulate or provide a gradient in the pressure applied to the periwound region. A biocompatible adhesive may secure the support cushion around the wound and the periwound region; and a biocompatible adhesive may secure the wicking strip in the periwound region between the wound and the support cushion.

In some embodiments, the reservoir may include a first hydrophilic layer, a non-stretchable mesh or scrim, and a second hydrophilic layer. In other embodiments, the reservoir may include a vent or vents that control humidity over the wound. Further, the reservoir or support cushion may include a port or ports for applying negative pressure within the dressing to provide negative pressure wound therapy, or through which a lavage solution may be periodically injected and withdrawn.

In accordance with another aspect of the invention, a method for managing exudate from a wound surrounded by a periwound region is provided, and includes: surrounding the wound and the periwound region with a support cushion; applying a wicking strip in the periwound region between the support cushion and the wound; and applying a reservoir over the wicking strip, wherein the wicking strip transfers exudate from the wound to the reservoir. In some embodiments, the method includes substantially filling the periwound region between the support cushion and the wound with the wicking strip.

In other methods of the present invention, the support cushion may include a vertically profiled portion, with the method further including fitting the reservoir within the profiled portion of the support cushion to suspend the reservoir over the wound. In such embodiments, the support cushion may be hydrophobic and the wicking strip and the reservoir may be hydrophilic, or optionally a combination of hydrophobic and hydrophilic materials, the method further including inhibiting lateral flow of exudate out of the reservoir and the wicking strip.

Still other methods of the present invention are designed to stimulate exudate flow by arranging the reservoir to compress the wicking strip, thereby applying a mild pressure in the periwound region that encourages exudate to migrate out of the wound and into the wicking strip. The wicking strip also may have a length and a height that varies along the length, such that the variation in height induces a pressure gradient in the periwound region when the reservoir is urged into engagement with the wicking strip. In some methods, the pressure gradient may be induced by applying a compression wrap over the dressing. A medication may be applied to the wound before applying the reservoir.

In still other embodiments, the method further may secure a cover to the support cushion with a biocompatible adhesive so that the adhesive urges the reservoir into engagement with the wicking strip. The method may further include securing the support cushion around the wound and the periwound region with a biocompatible adhesive; and securing the wicking strip in the periwound region between the wound and the support cushion with a biocompatible adhesive.

In accordance with yet another aspect of the present invention, a kit for use in managing exudate from a wound surrounded by a periwound region is provided and includes: a support cushion for surrounding the wound and the periwound region; a wicking strip configured to be applied in the periwound region between the support cushion and the margin of the wound; a reservoir configured to be applied over, and in engagement with, the wicking strip; a backing upon which the support cushion, wicking strip, and reservoir are mounted; and printed instructions for using the support cushion, wicking strip, and reservoir on a patient.

V. BRIEF DESCRIPTION OF THE DRAWINGS

FIGS. 1A and 1B and are an exploded view and a cross-sectional view, respectively, of an exemplary dressing of the present invention, while FIG. 1C is a partial sectional view illustrating transfer of exudate from the wound to the reservoir via the wicking strip.

Figure 4:
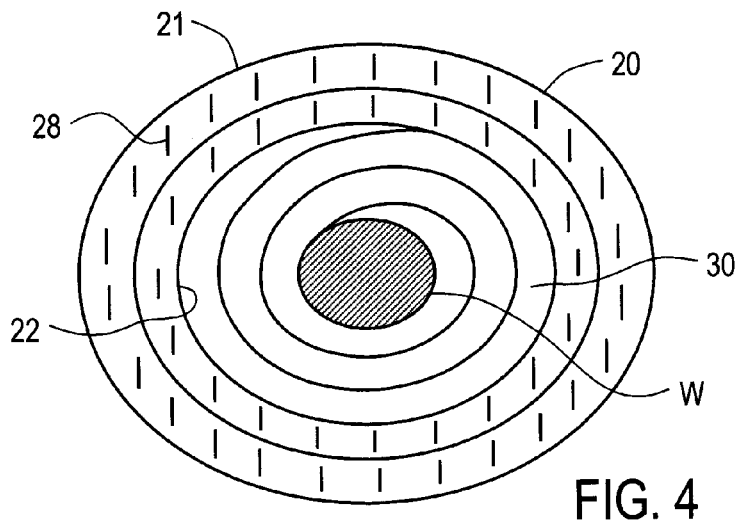

FIG. 4 schematically illustrates a plan view of one preferred embodiment of the support cushion and wicking strip.

Figure 5A:
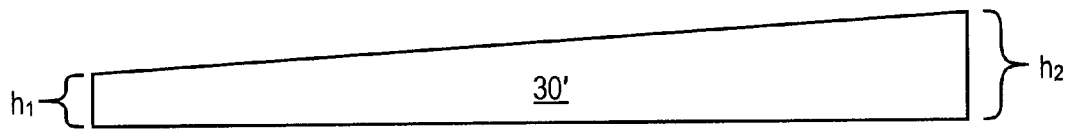
Figure 5B:
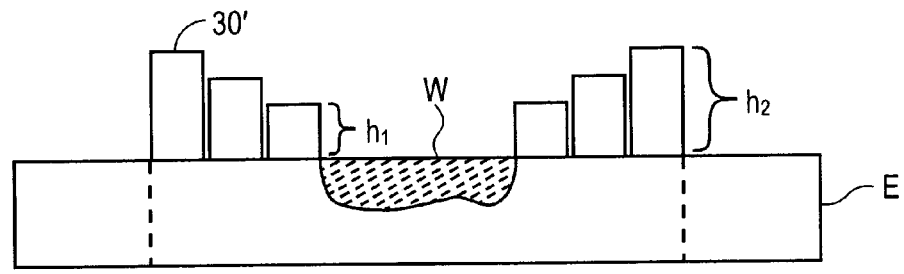
Figure 5C:
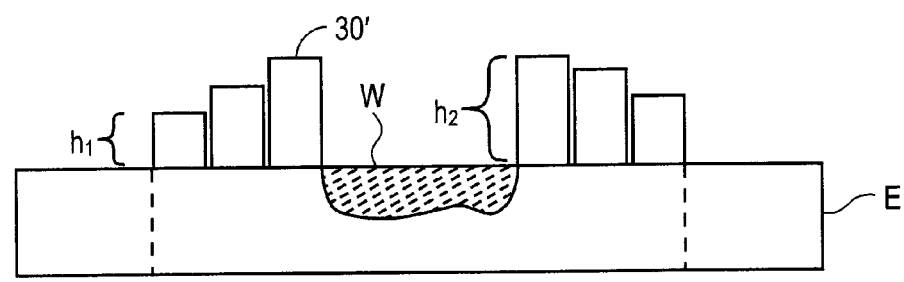

FIGS. 5A-5C illustrate alternative embodiments of a wicking strip suitable for use in the exudate management system of the invention.

Figure 6A:
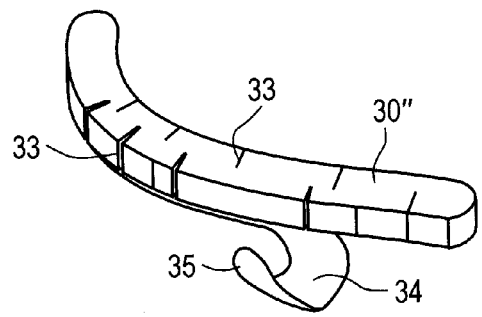
Figure 6B:
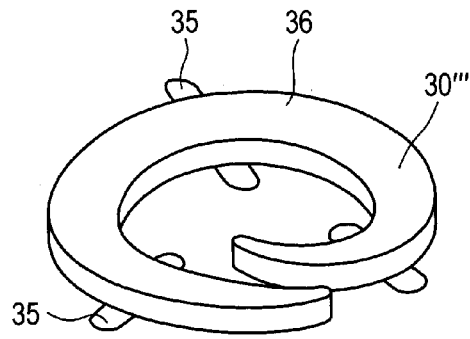

FIGS. 6A-6B illustrate further alternative embodiments of a wicking strip suitable for use in the exudate management system of the invention.

Figure 7:
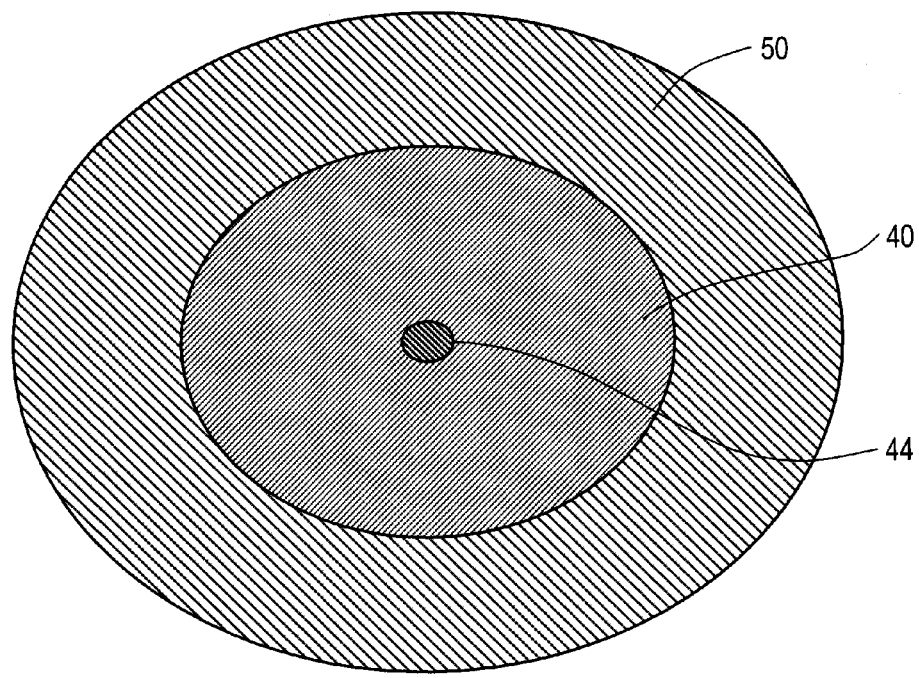

FIG. 7 schematically illustrates a plan view of a reservoir, cover, and optional vent according to some embodiments of the invention.

Figure 8:
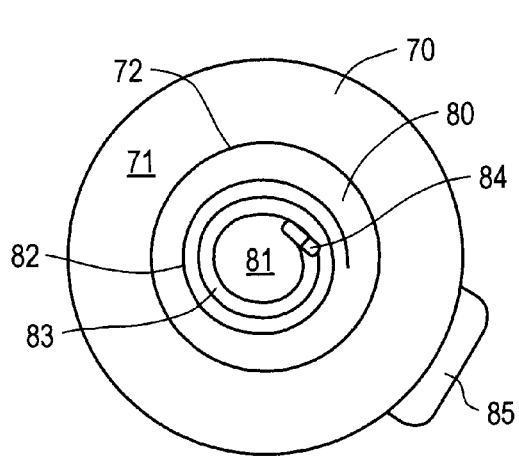

FIG. 8 is a plan view of an alternative embodiment of the support cushion and wicking strip of the present invention.

Figure 9:
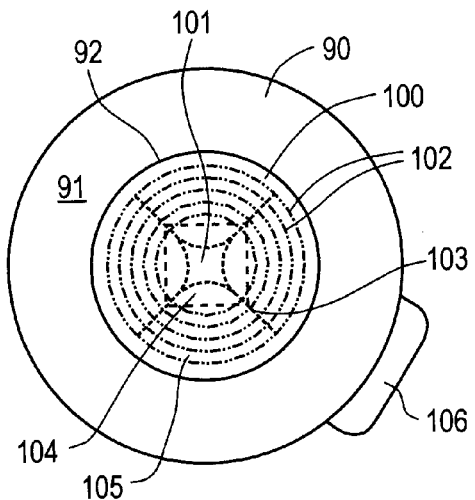

FIG. 9 is a plan view of another alternative embodiment of the support cushion and wicking strip of the present invention.

Figure 10:
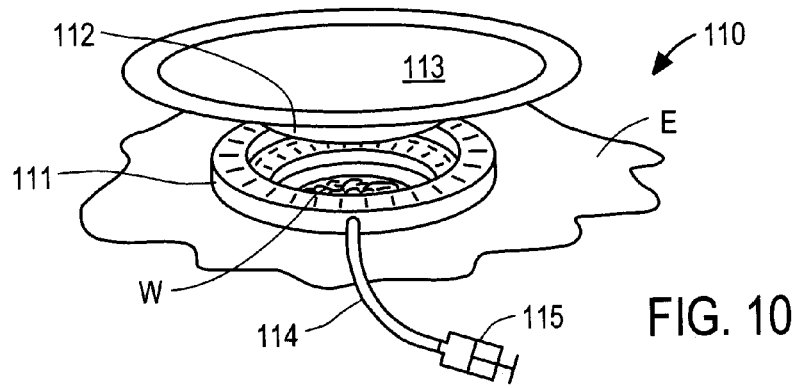

FIG. 10 is a perspective view of an alternative embodiment of the exudate management system of the invention including a lavage system, in which the wicking strip has been omitted for improved clarity.

Figure 11:
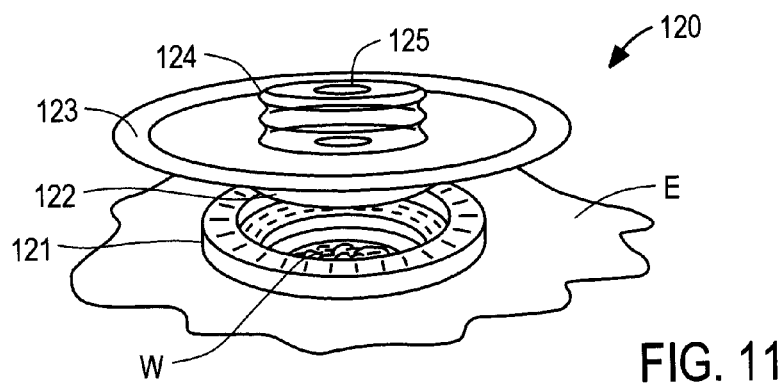

FIG. 11 is a perspective view of another alternative embodiment of the exudate management system of the invention including a manually-operated bellows for applying a negative pressure within the dressing.

FIGS. 12A and 12B are an exploded view, and a partial sectional view, respectively of another alternative embodiment of the dressing of the present invention.

FIGS. 13A and 13B are a plan view and perspective view, respectively, of an alternative embodiment of a cover and reservoir constructed in accordance with one aspect of the present invention.

Figure 14:
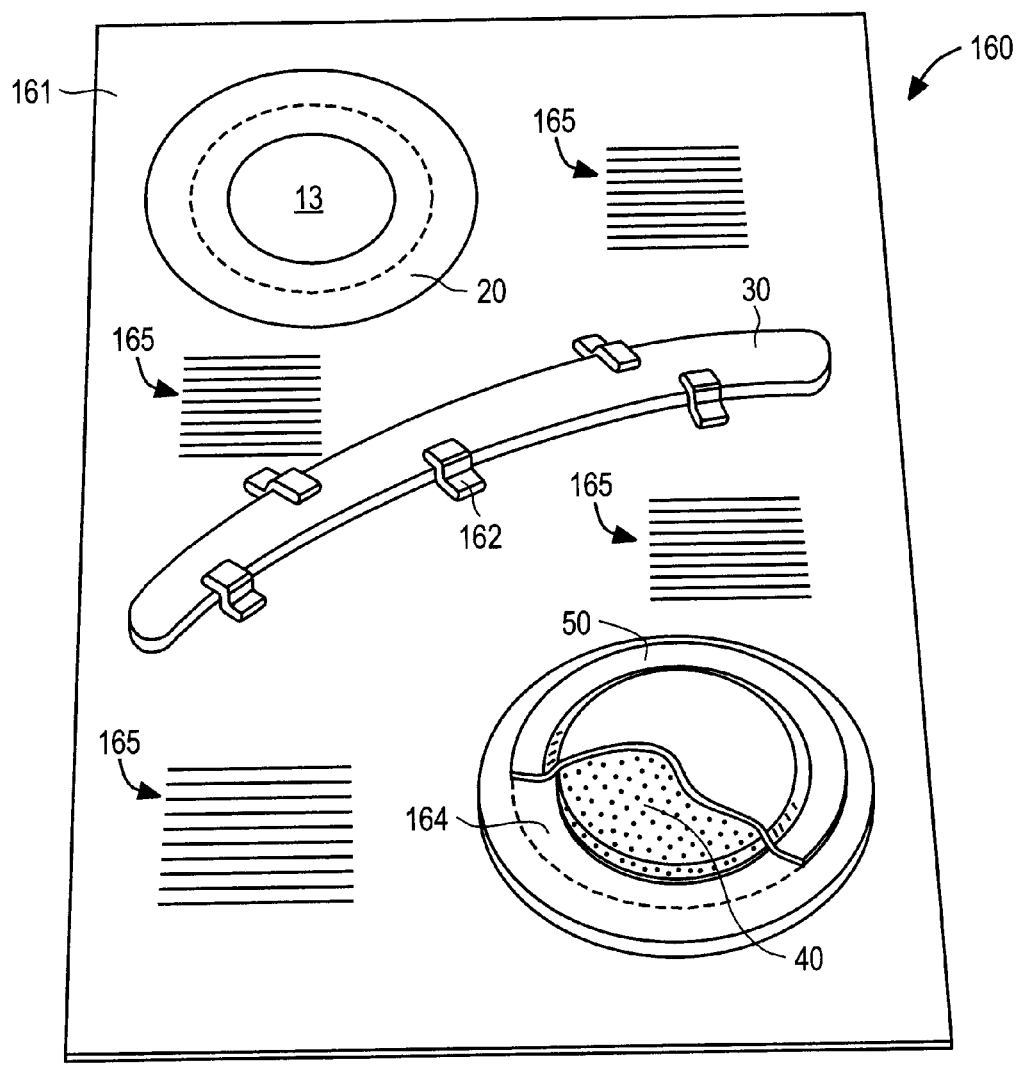

FIG. 14 schematically illustrates a plan view of a kit containing a system for exudate management, according to some embodiments of the invention.

VI. DETAILED DESCRIPTION OF THE INVENTION

The present invention provides systems and methods for protecting and promoting wound healing by managing exudate released by the wound. Among other things, the systems and methods provide a wound dressing that allows a wound to remain moist, while at the same time transferring excess exudate away from the wound and periwound region to a separately located reservoir. In this manner, the wound does not come into prolonged contact with excess exudate and periwound will not come in contact with any exudate, and thus both are protected from maceration or bacterial action that degrades tissue and skin. Unlike previously-known dressings, a dressing constructed in accordance with the principles of the present invention includes a reservoir that is elevated above the wound, and thus does not continuously contact the wound. This arrangement promotes wound healing by reducing the disruption of the wound bed (and pain) caused by periodic replacement of previously-known dressings, such as gauze, which adhere to the wound bed.

The systems and methods of the present invention also allow the flow of exudate from the wound to be managed by manipulating the amount and profile of pressure applied to the periwound skin, which also is expected to enhance the rate of healing of the wound.

An overview of an exemplary embodiment of a system for exudate management constructed in accordance with the principles of the present invention is first described, as well as a method of applying and using that system. Further details on the individual components employed in the system of the present invention, and alternative embodiments and methods, are described.

Overview of System

Figure 1A:
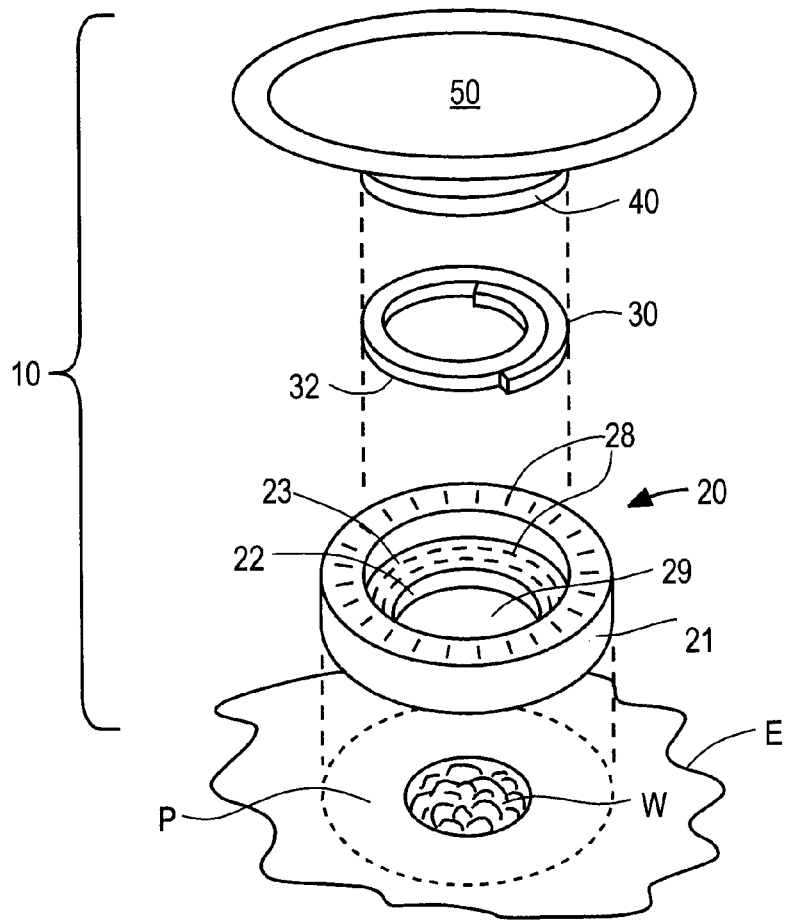
Figure 1B:
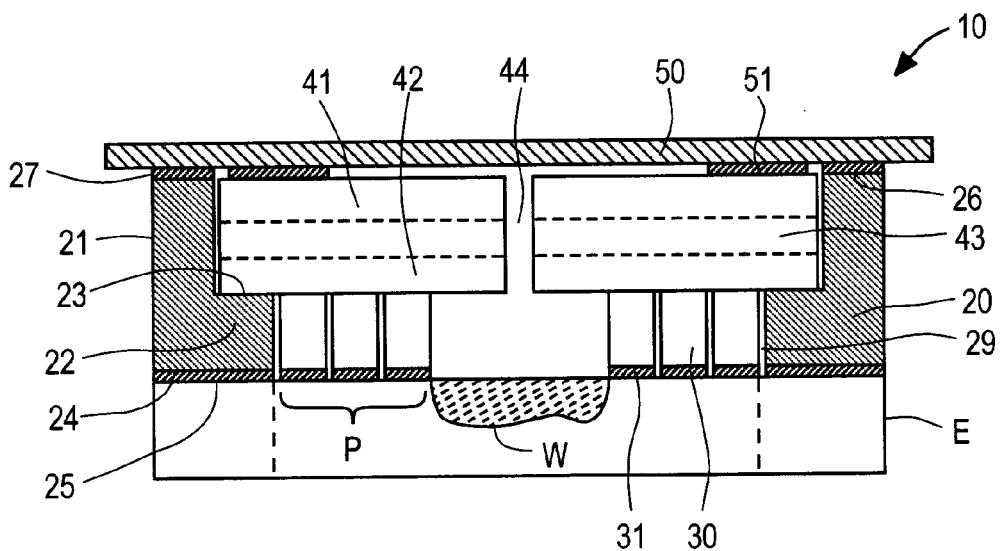

Referring now to FIGS. 1A and 1B, an exemplary embodiment of wound dressing 10, constructed in accordance with the principles of the present invention to provide exudate management, is described. In this exemplary embodiment, dressing 10 comprises three discrete components that are assembled and applied by the patient, nurse, clinician or other caregiver over wound W in patient's epidermis E. In particular, dressing 10 includes support cushion 20, wicking strip 30, and reservoir 40, preferably pre-attached to cover 50. Preferably, components 20, 30, 40 and 50 of dressing 10 are sized for use with one another and are enclosed in a sterile package with suitable instructions to enable the patient or caregiver to quickly and accurately apply the dressing. Alternatively, because for some embodiments certain components of dressing 10, such as wicking strip 30 and/or reservoir 40, may be replaced on a frequent basis than other portions of the dressing, such components may be individually packaged.

Support cushion 20 preferably comprises a closed cell polyolefin foam and is designed to surround wound W and periwound region P, i.e., the region of epidermis E extending from the wound margin, to protect the wound and elevate reservoir 40 and cover 50 above the wound bed. In the exemplary embodiment of FIG. 1, support cushion 20 has a stepped profile, including sidewall 21 and flange 22. The upper surface of flange 22 forms ledge 23 that supports reservoir 40, as depicted in FIG. 1B. Lower surface 24 of support cushion 20 includes layer 25 of biocompatible adhesive, which preferably is hydrophobic and breathable, while upper surface 26 includes layer 27 of adhesive or a portion of a reusable fastening system, e.g., the pile of a hook and pile fastening system, such as Velcro. Use of a non-permanent adhesive for layer 27 permits the cover to be removed to periodically replace wicking strip 30 and/or reservoir 40, as described below. In addition, support cushion 20 preferably includes slits or perforations 28 that extend through the heights of sidewall 21 and flange 22 to facilitate the escape of perspiration from beneath support cushion 20 when is it fastened by layer 25 to epidermis E. Support cushion 20 includes opening 29 that exposes a portion of the periwound region P extending away from the margin of wound W, to permit placement of wicking strip 30, as depicted in FIG. 1B.

Wicking strip 30, which preferably comprises an open-cell polyurethane foam, overlays periwound region P between the margin of wound W and flange 22 of support cushion 20. In the embodiment of FIG. 1, wicking strip 30 is depicted as a curved strip of foam, although it takes other forms as described herein for alternative embodiments. Wicking strip 30 preferably includes layer 31 of biocompatible adhesive, which preferably is hydrophobic and breathable, on lower surface 32. During application, wicking strip 30 may be rolled to a tighter spiral than depicted in FIG. 1A that it fits snugly within opening 29 of support cushion 20 and the innermost edge of the wicking strip preferably overlaps the margin of the wound by 1-2 mm. For the embodiment of FIG. 1A, wicking strip 30 may be cut with a scissor to ensure that the foam is not overly compressed when adhered to the periwound region by layer 31. In a preferred embodiment, establishing snug contact between the outermost edge of wicking strip 30 and the inner-facing surface of flange 22 ensures that exudate does not leak onto an exposed portion of the periwound region between wicking strip 30 and support cushion 20. Alternatively, outer-facing surface 32 of wicking strip 30 may employ a hydrophobic film or coating that prevents exudate from seeping into the periwound region.

Still referring to FIG. 1, reservoir 40 preferably comprises a sandwich of different density open cell polyurethane foams 41 and 42 joined to mesh 43, in which the foams 41 and 42 are selected to absorb exudate from wicking strip 30 and to sequester the exudate away from the wound bed. In the embodiment depicted in FIG. 1, reservoir 40 is fastened to the underside of cover 50, and is sized so that the outer edges of the reservoir are supported on ledge 23 of support cushion 20, while the more central regions of the reservoir engage the upper surface of wicking strip 30. Preferably, reservoir 40 fits within sidewall 21 of support cushion 20, so that exudate drawn into the reservoir from wicking strip 30 cannot seep out of the lateral face of the reservoir. As shown in FIG. 1B, flange 22 suspends reservoir 40 over wound W, thus inhibiting contact between reservoir 40 and wound W and limiting the extent to which force applied to cover 50 and reservoir 40 is transmitted to wicking strip 30. Wicking strip 30 may additionally support reservoir 40 over wound W. Optionally, a layer of adhesive may be disposed on the lower surface of the reservoir 40 that engages ledge 23 of the support cushion to removably secure those components together. Reservoir 40 preferably includes one or more vents 44 that assist in modulating the humidity within the dressing through cover 50.

Cover 50, preferably a breathable material, overlays reservoir 40. Layer 51 of adhesive preferably is used to removably secure reservoir 40 to cover 50. Alternatively, reservoir 40 may be removably fastened to cover 50 using a removable fastening system, such as hook and pile arrangement. In addition, layer 27 of adhesive, or a removable fastening system, is used to secure cover 50 to the upper surface of sidewall 21 of support cushion 20, so that cover 50 and/or reservoir 40 may be periodically removed from dressing 10 to inspect the wound, to apply topical medications or other substances to the wound, e.g., moisturizing ointments, growth factors, nutrients, and/or antibiotics, or to replace wicking strip 30 or reservoir 40. In other embodiments, cover 50 and/or reservoir 40 are left in place over the wound while dressing 10 is applied to the patient.

As described in greater detail below, the components of dressing 10 may each be provided with one or more non-stick liners to facilitate handling of the different components of the system, e.g., while placing support cushion 20 on epidermis E. The liners may be removed as appropriate to expose the adhesive layers and secure components to epidermis E or to each other.

Figure 1C:
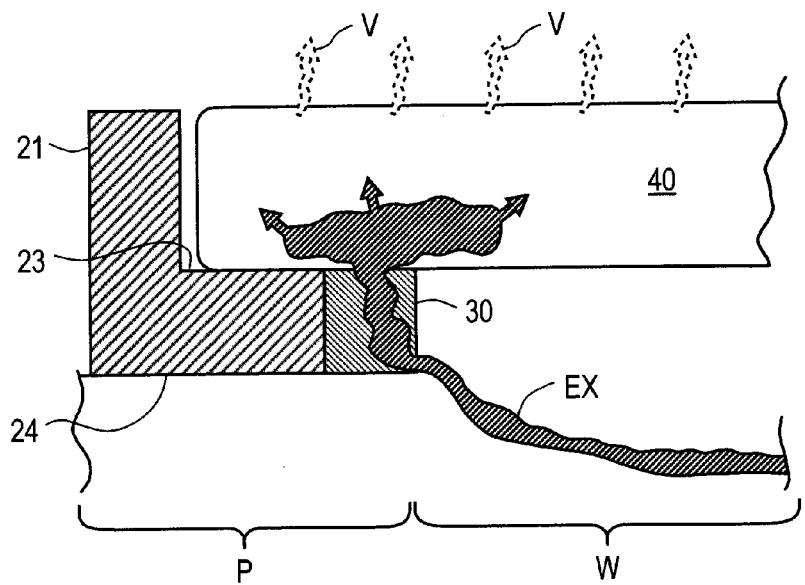

Referring now to FIGS. 1B and 1C, during use of dressing 10, exudate EX flows out of wound W at a flow rate that depends on many factors, including the pressure with which wicking strip 30 is pressed against the periwound region, the lateral profile of wicking strip 30 (described in greater detail below with reference to FIGS. 5A-5C), the characteristics of wound W, and the consistency of the exudate. As exudate EX is released from the wound, some of the exudate pools on top of wound W. As discussed above, such accumulation of excess exudate with high concentrations of MMPs leads to degradation of extracellular matrix protein both in the wound and on periwound skin. However, excess exudate may flow from the wound, or gravity and/or patient movement may displace exudate from the wound bed so that it contacts and is absorbed by wicking strip 30.

As depicted in FIG. 1C (from which cover 50 has been omitted for clarity), wicking strip 30 transports exudate EX laterally (in the plane of epidermis E) and then vertically (perpendicular to the plane of epidermis E) to reservoir 40. Specifically, the exudate travels along a gradient from relatively wet regions to relative dry regions of the wicking strip via capillary action. Exudate transported laterally may eventually reach the inner surface of flange 22 of support cushion 20. Because support cushion 20 is formed of a hydrophobic material, it inhibits further lateral transport of the exudate. Instead, exudate preferably is transported vertically from wicking strip 30 and into reservoir 40, which sequesters exudate away from the wound. In accordance with one aspect of the invention, reservoir 40 preferably has a large absorptive surface area and the capacity to hold large amounts of exudate, e.g., sufficient capacity so that reservoir 40 need only be replaced once every few days (for example, every 7-10 days). Reservoir 40 is also breathable, so that it releases water in the exudate in the form of vapor V into the atmosphere via breathable cover 50. Additionally, ledge 23, upon which reservoir 40 rests, and sidewall 21, adjacent to reservoir 40, are hydrophobic and cannot transfer exudate from reservoir 40 onto the periwound region. Accordingly, dressing 10 is configured to inhibit prolonged contact between the exudate and periwound region, and thus to inhibit maceration or other degradation of the periwound region, as observed with previously-known dressings.

Multiple features of dressing 10 both enhance the healing of wound W and protect periwound region P from maceration and degradation. Among other things, although reservoir 40 is arranged to protect the wound from the environment and absorb exudate, it is suspended over and thus is not in continuous contact with the wound. This feature may both reduce any pain experienced by the patient and promote healing. For example, initially placing reservoir 40 (and the other components of dressing 10) does not require touching the wound bed itself, resulting in significantly less pain than, for example, than the V.A.C.® or systems similar to it described above that rely on inserting a sponge or gauze directly into the wound. Wicking strip 30 and/or reservoir 40 also may readily be removed without disrupting re-epithelialization of the wound. Moreover, because reservoir 40 sequesters the exudate, when reservoir 40 is removed to observe the wound, exudate does not flow onto the adhesive used to secure cover 50 to support cushion 20. This arrangement allows wicking strip 30 and/or reservoir 40 to be replaced and for cover 50 to be re-secured to support cushion 20, without having to replace the entire dressing. By contrast, removing previously known dressings (which contact the wound) often disrupts re-epithelialization and allow exudate to flow onto the adhesive, requiring the entire wrap to be discarded and a new one applied.

It is noted that although reservoir 40 is designed to be suspended over, rather than in contact with the wound, occasions may arise where the reservoir will contact the wound. For example, if sufficient pressure is applied directly onto cover 50 and reservoir 40, the reservoir may deflect sufficiently to contact the wound for as long as that pressure is applied. Such temporary contact is not believed to significantly impede the healing of the wound, and the durometer and resiliency of support cushion 20 preferably is selected to provide adequate support for cover 50 and reservoir 40 in the expected range of applications.

Dressing 10 also encourages the flow of exudate from the wound, and thus reduces the bacterial load of the exudate in contact with the wound bed. Without wishing to be limited by theory, the inventors believe that the flow of exudate from the wound may stimulate healing. First, dressing 10 encourages exudate flow by continuously wicking exudate out of the wound, thereby providing a lower osmotic pressure at the wound than in the surrounding tissue. This osmotic pressure differential encourages exudate to flow from the surrounding tissue into the wound to attempt to equalize the osmotic pressure. In contrast, conventional dressings that directly contact the wound typically do not generate an osmotic pressure differential. In addition, because dressing 10 absorbs exudate from the wound and promotes replenishment of exudate, the bacterial load of the exudate in contact with the wound bed remains relatively low. Dressing 10 also is configured to allow a variety of different types of pressure to be applied to the periwound region, depending on the type of wound, as described in greater detail below with respect to FIGS. 5A-5C.

Additionally, dressing 10 is well-suited for use in treating pressure sores that may be acquired by patients whose skin may be damaged by, for example, continuously lying in bed without sufficient movement. Such pressure sores may occur where skin is thin, has reduced integrity, and/or where bone and skin are close together, without sufficient intervening muscle or fat. Support cushion 20 rests on regions of epidermis E that surround the wound, thus protecting the wound from the type of pressure that initially caused the wound. Support cushion 20 may be formed of a supple, easily bendable material that does not create a pressure ring around the wound. In some embodiments, support cushion 20 is formed of a polyolefin that distributes pressure, inhibiting that pressure from concentrating in one region.

Overview of Method

Figure 2:
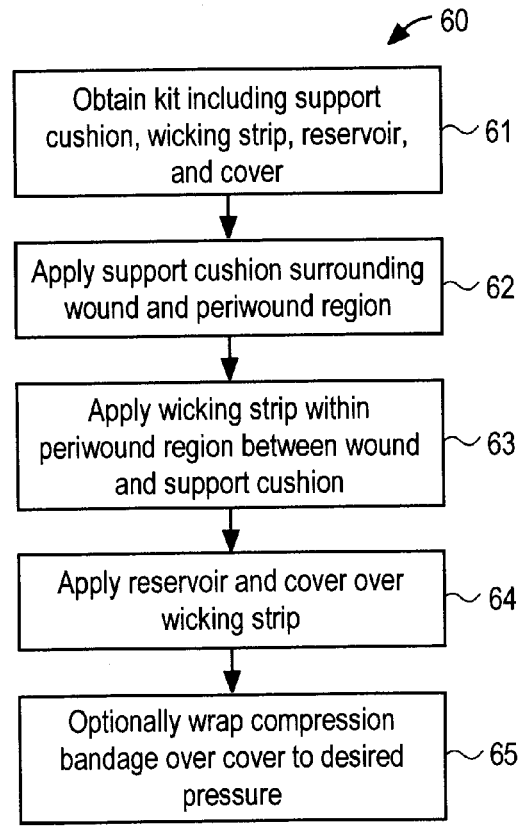
FIG. 2 illustrates steps in accordance with one method of the present invention for exudate management.

FIG. 2 illustrates steps in a method 60 of using dressing 10 for managing exudate from a wound, according to some embodiments of the invention. Typically, the method is implemented by a physician, nurse, or other caregiver. However, the method is relatively simple to employ, and the patient himself may apply dressing 10.

First, at step 61, the caregiver obtains support cushion 20, wicking strip 30, reservoir 40, and cover 50, e.g., a kit as described below with respect to FIG. 7. Next, in step 62, support cushion 20 is applied to the epidermis of a patient, so that the support cushion surrounds the wound and periwound region. For example, a non-stick liner covering lower surface 24 of support cushion 20 may be removed to expose the adhesive on its lower surface. The support cushion then is roughly centered around the wound, and pressed onto the patient's epidermis using gentle manual pressure. A non-stick liner covering layer 27 on the upper surface of support cushion 20 may be left in place until a later step, described below.

At step 63, wicking strip 30 is applied within the periwound region between the margin of the wound and support cushion 20. For example, wicking strip 30 will include a non-stick liner covering layer 31, and this liner will be removed to expose the adhesive. A first end of wicking strip 30 then is applied and adhered to a first portion of the periwound region, e.g., just overlapping the margin of the wound. The free end of the wicking strip then is spiraled around the wound, with subsequent portions of wicking strip 30 adhered to adjacent portions of the periwound region, for example, as illustrated in FIG. 4, until the entirety of the periwound region exposed within opening 29 of the support cushion is filled. Preferably, wicking strip 30 fills substantially the entire periwound region between the wound and support cushion 20, to prevent seepage of exudate from the outermost lateral face of the wicking strip. In some circumstances, the wound may be sufficiently large that the entire wicking strip 30 is not needed to fill the periwound region between the wound and support cushion 20, in which case wicking strip 30 may be cut to the appropriate length. The wound may have a relatively irregular shape, and simply spiraling wicking strip 30 around the wound will adequately fill the entire periwound region. Alternatively, wicking strip 30 may be cut into multiple pieces of appropriate lengths, which are individually adhered to the periwound region as appropriate.

At step 64, reservoir 40 and cover 50 (which is preferably pre-adhered to reservoir 40) then are applied over wicking strip 30. For example, the non-stick liner may be removed from layer 27 disposed on the upper surface of side wall 21, and reservoir 40 inserted into support cushion 20 so that the exposed adhesive on support cushion 20 adheres to cover 50, as illustrated in FIG. 1B.

Figure 3:
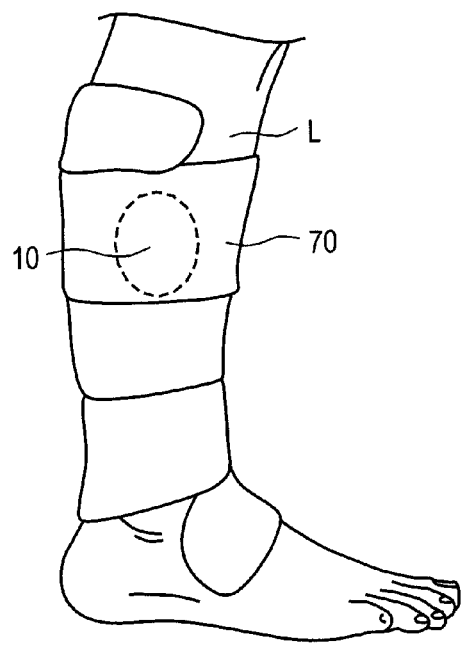
FIG. 3 illustrates a perspective view of an illustrative application of the inventive dressing of FIG. 1 to a patient.

At step 65, compression wrap 70 optionally is wrapped over dressing 10 to apply a desired pressure onto the dressing and wound, e.g., as illustrated in FIG. 3. For example, as discussed above, the amount of applied pressure may affect the flow of exudate and the rate of healing of the wound, so the physician may elect to compress dressing 10. The appropriate amount of pressure and wrap type may differ from wound to wound, and may be selected based on the physician's knowledge and experience with particular wound types. Elastic compression wraps such as PROFORE® (Smith & Nephew, Largo, Fla., USA) may suitably be used.

For example, if using an elastic compression wrap to compress dressing 10 against a venous leg ulcer, the wrap may be stretched beyond a specified proportion of its native length, and then secured in that stretched configuration. The physician optionally may apply other wraps on dressing 10, such as gauze or Unna Boot or both. Such intervening layers of material also may be applied with compression, as appropriate.

Some wound sites located on broad surfaces, such as the torso, may not easily be wrapped with a compression wrap, in which case the differential heights between the support cushion, reservoir and wicking strip of dressing 10 may be adjusted to provide sufficient pressure to stimulate the flow of exudate. For example, as described herein after with respect to the embodiment of FIGS. 5A to 5C, a wicking strip having a variable height may be employed with the dressing of the present invention. Depending upon how the wicking strip is applied surrounding the wound, the dressing and compression wrap, if present, may be adjusted to provider either greater or lesser pressure on the tissue surrounding the wound, or to provide a uniform pressure at the wound site in view of complex limb topology.

Optionally, a medication or other substance may be applied to the wound or periwound region during any appropriate step in method 60. For example, the wound and periwound region may be cleaned, dried, and/or debrided or moisturized before applying support cushion 20 to the epidermis. Or, for example, a wound dressing such as PROMOGRAN PRISMA™ collagen and silver dressing (available from Systagenix Wound Management, London, UK), or Dermagraft® (available from Advanced BioHealing, La Jolla, Calif., USA), or Apligraf® (available from Organogenesis, Inc., Canton, Mass., USA), and other similar collagen or biological dressings, may be applied to the wound after applying wicking strip 30, but before applying reservoir 40 and cover 50. Other substances may be used, such as time-release topical medicines.

Further details of the construction of the individual components of dressing 10, and alternative embodiments, are now provided.

Support Cushion 20

Referring to FIG. 4, support cushion 20 and wicking strip 30 are further described. Support cushion 20 includes sidewall 21 and flange 22, which forms ledge 23. Each of sidewall 21 and flange 22 includes plurality of slits 28 that enhances its breathability and flexibility. In particular, slits 28 may be arranged radial or circumferential directions, or with another preferred orientation to improve conformability of the support cushion to the anatomy of a specific limb. Support cushion 20 preferably is secured to patient's epidermis using a biocompatible adhesive layer, which is preferably hydrophobic but breathable, or alternatively, may be secured using a compression wrap that overlays the dressing.

In some embodiments, support cushion 20 is of unitary construction, with sidewall 21 and flange 22 being formed from different portions of the same piece of material. Alternatively, sidewall 21 and flange 22 may be individually constructed and then heat-fused or adhesively bonded together, thus allowing the materials, thicknesses, and other characteristics of sidewall 21 and flange 22 to be selected tailored for specific applications. For example, it may be preferable to form sidewall 21 using a relatively thick layer of a large-cell hydrophobic material and flange 22 using a relatively thin layer of a small-cell hydrophobic material. Such a combination of materials and thicknesses imparts support cushion 20 with sufficient flexibility to be conformable to substantially any body part, e.g., an arm, leg, neck, or torso, while maintaining a sufficient level of hydrophobicity to prevent exudate from leaking onto the periwound region. Examples of suitable hydrophobic materials for use in support cushion 20 include polyolefin, foams, and silicone-based materials, in open cell or closed cell forms. Any suitable adhesive or bonding procedure can be used to adhere sidewall 21 to flange 22.

As mentioned above, slits 28 may enhance the flexibility and breathability of support cushion 20, e.g., to allow support cushion 20 to more readily conform to various body parts and to allow humidity in the regions of the epidermis underlying support cushion 20 to escape, thus reducing maceration. Slits 28 may be simple "cuts" that extend through support cushion 20, e.g., through sidewall 21 and flange 22, without removing material. Alternatively, slits 28 may be apertures formed by removing material from sidewall 21 and/or flange 22. Slits 28 may be formed in any appropriate size, shape, density, or pattern. For example, slits 28 may extend in a single direction, as illustrated in FIG. 4, may extend radially (perpendicular to curvature of support cushion 20), may extend parallel to the curvature of support cushion 20, or may extend at an angle relative to the curvature of support cushion 20. Some slits 28 may extend at different angles than other slits 28.

Alternatively, support cushion 20 of the present invention may comprises a spacer fabric, such as the polyester/nylon spacer fabric designated style DNB69, available from Apex Mills, Inward, N.Y., USA. Such materials are hydrophobic, but include an open weave that is highly breathable, thereby permitting moisture to readily evaporate from the patient's skin during prolonged use, while preventing maceration.

In the embodiment illustrated in FIG. 4, support cushion 20 is pre-formed in a generally oval shape, and is suitable for use with wounds up to a fixed size, e.g., up to 30 mm in length. However, support cushion 20 also may be formed in any other appropriate shape and size and may be provided having a range of size of openings 29 in flange 22. For example, support cushion 20 may be pre-formed in a generally circular, rectangular, triangular, or other polyhedral shape, optionally having rounded corners, or may even be pre-formed in an irregular shape. Alternatively, support cushion 20 may be formed as a strip that may be applied around the wound and periwound region. The strip may be of predetermined length, or may even be provided on a roll and cut to a desired length. In such embodiments, it may be convenient to apply support cushion 20 to the epidermis after wicking strip 30 is applied around the wound.

To accommodate such free-form embodiments of the support cushion, it may be desirable for reservoir 40 and cover 50 to have a basket-like configuration, such as described in detail below with respect to FIG. 13.

In still other embodiments (not illustrated), support cushion 20 may be an annular structure filled with a fluid, e.g., air or water, a gel, an expanded plastic, or fibers. Such structure may be formed of molded plastic, welded polymer, or a laminate.

Wicking Strip 30

In the embodiment illustrated in FIG. 4, wicking strip 30 is an elongated strip of hydrophilic material spiraled around wound W in the space between the wound and the inner surface of flange 22. Preferably, wicking strip 30 is sufficiently flexible that it may be applied in any desired pattern to the epidermis, e.g., that it may be packed so as to fill substantially the entire space between the wound and the innermost surface of defining opening 29 of support cushion 20. One example of a suitable hydrophilic, flexible material for use in wicking strip 30 is an open-cell foam such as hydrophilic polyurethane. Alternatively, wicking strip 30 may include any suitable absorbent structure, e.g., a woven fabric, a nonwoven fabric, a hydrogel (which may include modified starch), or a pouch filled with a polymeric absorbent material.

In the embodiment of FIG. 1, wicking strip 30 is depicted as having the same height as flange 22 of support cushion 20. However, wicking strip 30 may actually have a different height than flange 22, but reservoir 40 may compress the two components to the same height during use. For example, wicking strip 30 may be thicker or thinner (taller or shorter, respectively) than flange 22, and may have a different compliance. In one embodiment, wicking strip 30 is thicker than flange 22, but is more easily compressed, allowing both components to be compressed to the same thickness by reservoir 40 during use.

Likewise, wicking strip 30 may have a variable width along its length, as depicted in FIG. 1A. In other embodiments, such as that depicted in FIG. 4, the width of wicking strip 30 is essentially constant along its length. Referring to FIG. 5A, an embodiment of a wicking strip is depicted wherein a first end of wicking strip 30' has a first height $h_1$, and a second end a second height $h_2$, wherein $h_1$ is less than $h_2$. As illustrated in FIG. 5B, the asymmetrical-height wicking strip 30' may be applied to the periwound region with the first, shorter end adjacent to the wound and the second, taller end furthest from the wound. When reservoir 40 is compressed onto wicking strip 30' in this arrangement, wicking strip 30' will apply a lower pressure adjacent the wound, due to the smaller amount of material being compressed, and a higher pressure further from the wound, due to the greater amount of material being compressed in that region. While compressed, wicking strip 30' may appear to have the same height along its length, even though its thickness varies in its native (non-compressed) state. Alternatively, as illustrated in FIG. 5C, wicking strip 30' may be applied to the periwound region with the second, taller end adjacent the wound and the first, shorter end furthest from the wound. When reservoir 40 is compressed onto wicking strip 30' in this arrangement, wicking strip 30' will apply a higher pressure adjacent the wound, due to the greater amount of material being compressed, and a lower pressure further from the wound, due to the smaller amount of material being compressed. The arrangement of such an asymmetrical wicking strip 30' may be selected based on the type of wound being treated. For example, pressure wounds may benefit from a lower pressure being applied near the wound, whereas venous leg ulcers may benefit from a higher pressure being applied near the wound. Other types of wounds may benefit from different pressure gradients being applied. In many embodiments, wicking strip 30 is composed of a supple material that, when pressure is applied to it, does not create a potentially harmful pressure ring around the wound.

As illustrated in FIGS. 4 and 5A-5C, the wicking strip may have a relatively even width along its length. However, the wicking strip of the present invention also may be provided in a variety of other shapes and sizes, depending on the intended application. FIG. 6A illustrates an embodiment in which wicking strip 30" is additionally provided with relaxation cuts 33 that enhance its lateral flexibility, thereby facilitating lateral bending without buckling or crimping. Non-stick liner 34 is attached to layer 25 of adhesive, and may include tabs 35 that facilitate application of the wicking strip.

FIG. 6B illustrates an embodiment in which wicking strip 30''' is pre-formed in a bowed or arcuate shape, optionally including wider thicker portion 36, which may facilitate application of the wicking strip around the wound by reducing the lateral bending required to surround the wound. The degree to which wicking strip 30''' is bowed may vary, depending on the size of the wound with which it is intended to be used, and the compliance of the material. For example, wicking strip 30''' may be highly bowed, e.g., formed to be a spiral in its native configuration (before adhesion to the epidermis). FIG. 6B also illustrates tabs 35, which are part of or attached to non-stick liner 34 and may facilitate removal of the liner, which may optionally be included in any embodiment of wicking strip 30.

In still other embodiments (not illustrated), the wicking strip is pre-formed into an annular form. If the inner boundary of such an annular form does not come sufficiently close to the border of the wound to protect the periwound region, then additional pieces of wicking strip may be applied in the gap between the annular form and the margin of the wound.

Reservoir 40

As illustrated in FIG. 1, reservoir 40 may include multiple layers bonded together or alternatively may be formed of a single, hydrophilic layer. In the embodiment of FIG. 1, reservoir 40 includes upper layer 41, lower layer 42 and intervening layer 43. Lower layer 42 engages the upper surfaces of wicking strip 30, and transfers exudate through intervening layer 43, and into upper layer 41. Although reservoir 40 is composed of breathable material that allows for the transfer of moisture vapor as needed, reservoir 40 optionally may contain vent 44 that extends through the reservoir to provide a less impeded route for moisture vapor transfer.

Referring again to FIG. 1B, both upper layer 41 and lower layer 42 are hydrophilic. However, layers 41 and 42 may have the same or different hydrophilicities, mechanical properties, transfer rates for exudate, and capacities for absorbing exudate. In some embodiments, layers 41 and 42 are formed from hydrophilic polyurethane foams, e.g., commercially purchased polyurethane foams from Rynel, Inc. (Wicasset, Me., USA). The foam from which lower layer 42 is fabricated has a higher hydrophilicity than that of upper layer 41, allowing it to rapidly transfer exudate into upper layer 41. The polyurethane foams may be coated or interlaced with any suitable antibacterial or antimicrobial agents (e.g., silver) to combat or prevent infection.

Intervening layer 43 enhances the strength and stiffness of reservoir 40, making it more difficult to inadvertently deflect reservoir 40 downward to contact the wound. Intervening layer 43 may be, for example, a substantially non-stretchable mesh or scrim, such as a metallic, nylon, or polyester-based mesh.

In some embodiments, layers 41, 42, and 43 are co-selected to enable reservoir 40 to form a dome-like shape as it absorbs exudate and swells, while still maintaining contact with ledge 23 and sidewall 21 of support cushion 20. For example, intervening layer 43 may be formed to have a larger diameter than the diameter defined by the sidewall 21 of support cushion 20. As reservoir 40 absorbs exudate and swells, this difference in diameter allows intervening layer 43 to buckle upward.

Cover 50

Referring now to FIGS. 1B and 7, cover 50 is described having pre-fastened reservoir 40 with vent 44. Cover 50 may be adhered to upper layer 41 with a layer of adhesive, or otherwise attached to upper layer 41 before or after reservoir 40 is placed over the wound. During use, cover 50 is adhered to sidewall 21 using layer 27 of adhesive, which urges reservoir 40 against wicking strip 30. In some embodiments, cover 50 extends beyond the lateral dimensions of support cushion 20, so that when dressing 10 is applied to a patient, cover 50 drapes over support cushion 20 and covers layer 27 of adhesive. Such draping protects the edges of support cushion 20 from lifting, and additionally provides a smooth, comfortable surface over which clothing and bed linens may slide freely. In other embodiments, layer 27 may comprise a removable fastener, such as a hook and pile arrangement that enables the cover to be periodically removed to inspect the wound, apply medicaments, or to replace the wicking strip or reservoir.

Cover 50 is made of a soft, occlusive material that provides an antibacterial barrier between the wound and the environment, and also allows humidity to escape from reservoir 40 and vent 44. One example of a suitable material for cover 50 is Intelicoat 2327, available from Intelicoat Technologies (South Hadley, Mass., USA). The material may be coated or intercalated with any suitable antibacterial or antimicrobial agent to combat or prevent infection.

ADDITIONAL ALTERNATIVE EMBODIMENTS

Referring now to FIGS. 8 and 9, additional embodiments of the support cushion and wicking strips suitable for use in the dressing of the present invention are described, which simplify the construction and application of the dressings. In FIG. 8, support cushion 70 comprises sidewall 71 of uniform height defining opening 72 and wicking strip 80 disposed within opening 72. The upper surface of wicking strip 80 visible in FIG. 8 is recessed below the top of sidewall 71 of support cushion 70 to accept reservoir 40 and cover 50 as described with respect to preceding embodiments. Preferably, the height of wicking strip 80 is in a range of 40-60% of the height of sidewall 71. In this embodiment, wicking strip 80 is pre-adhered to support cushion 70 so that the lower surfaces of support cushion 70 and wicking strip 80 are flush, and includes opening 81 that may be used to visually position the unit over a wound. Wicking strip 80 includes spiral perforation 82 that extends through the height of the wicking strip, so that the perforation forms spiraled inner portion 83 of the wicking strip. The innermost end of the spiraled portion terminates at pull tab 84.

Support cushion 70 and wicking strip 80 preferably include a layer of adhesive on the lower surface, similar to layer 25 in the embodiment of FIG. 1B, which is covered by non-stick liner having removal tab 85. Support cushion 70 also includes layer 27 of adhesive or other suitable fastening means on its upper surface, and may include a plurality of slits 28, as described for preceding embodiments, to improve breathability and conformability of the support cushion. Reservoir 40 and cover 50, as described for preceding embodiments, may be employed, so that the reservoir fits snugly within the recess above wicking strip 80.

In the embodiment of the invention depicted in FIG. 8, spiraled portion 83 of wicking strip 80 is configured to be removed, using pull tab 84, to unwind the wicking strip to just expose the margin of the wound. The length of the spiraled portion 83 that is unwound to expose the margin of the wound then is cut off with a scissor and discarded. In this manner, the wicking strip may be easily positioned at the preferred location at the margin of the wound, with the remainder of wicking strip 80 covering the periwound region, thereby reducing the time required to apply the inventive dressing. Once the support cushion and wicking strip are positioned, and the appropriate length of spiraled portion 83 removed to expose the margin of the wound, the reservoir and cover then is fastened atop support cushion 70 and wicking strip 80 so that the reservoir is engaged with the upper surface of wicking strip 80.

In the embodiment of FIG. 9, support cushion 90 is configured similar to support cushion 70 of FIG. 8, and includes sidewall 91 of uniform height that defines opening 92. Wicking strip 100 is disposed within opening 92 so that its upper surface is recessed below the top of sidewall 91 to accept reservoir 40 and cover 50 as described with respect to preceding embodiments. Preferably, the height of wicking strip 100 is in a range of 40-60% of the height of sidewall 91 and is pre-adhered to support cushion 90 so that the lower surfaces of support cushion 90 and wicking strip 100 are flush. Wicking strip 100 includes opening 101 that may be used to visually position the unit over a wound, plurality of circular perforations 102 and illustratively, four radially-directed perforations 103 that divide the wicking strip into quadrants. Pull tabs 104 are connected to the innermost ring of the wicking strip in each quadrant. Perforations 102 and 103 extend through the height of the wicking strip, so that the perforations form arcs of predetermined length 105 that may be individually removed using pull tabs 104.

Support cushion 90 and wicking strip 100 preferably include a layer of adhesive on the lower surface, similar to layer 25 in the embodiment of FIG. 1B, which is covered by non-stick liner having removal tab 106. Support cushion 90 also includes a layer of adhesive or other suitable fastening means on its upper surface, and may include a plurality of slits, as described for preceding embodiments, to improve breathability and conformability of the support cushion. Reservoir 40 and cover 50, as described for preceding embodiments, may be employed.

In the embodiment of the invention depicted in FIG. 9, arcs 105 of wicking strip 100 are configured to be removed, using pull tabs 104, to remove the portion of the wicking strip up to the margin of the wound. Thus, the patient or caregiver would first remove the non-stick liner from the support cushion and wicking strip, and align it centered on the wound using opening 101. The patient or caregiver then would remove a selected, and perhaps unequal, number of arcs 105 from each quadrant using pull tabs to best approximate, or slightly overlap, the margin of the wound. The removed arcs 105 of wicking strip 105 then may be discarded. Once the support cushion and wicking strip are so applied, a reservoir and cover, as described for preceding embodiments, is fastened atop support cushion 90 and wicking strip 100 so that the reservoir is engaged with the upper surface of the wicking strip.

It should be understood that the dressing of FIG. 9 advantageously permits an uneven number of selected arcs 105 of the wicking strip to be removed from each quadrant, thereby enabling the patient or caregiver to best approximate irregularities in the margin of the wound. This in turn provides a high degree of protection of the periwound region, without the need to custom fit the entire length of the wicking strip to cover the periwound region between the support cushion and the margin of the wound, for example, as described with respect to FIG. 4. In addition, it should be understood that while the wicking strip 100 of the embodiment of FIG. 9 includes four radially-directed perforations, a greater or lesser number of such perforations may be provided, and that sectors defined by such perforations need not encompass equal areas.

Referring now to FIG. 10, a further alternative embodiment of the dressing of the present invention is described which provides the ability to periodically apply medications or to lavage wound W in epidermis E without disassembling dressing 110. Dressing 110 includes support cushion 111, a wicking strip as described with respect to preceding embodiments (omitted for clarity in FIG. 10), reservoir 112 and cover 113. The support cushion, wicking strip, reservoir and cover are constructed substantially as described for preceding embodiments. Dressing 110 differs from preceding embodiments in that support cushion 111 includes flexible tube 114 that may be permanently or removably inserted through the sidewall of the support cushion to deliver fluids, such as topical antibiotics or washing fluids through the sidewall to wound W, without needing to remove the reservoir and cover. Syringe 115 may be selectively coupled to the distal end of tube 114 to inject fluids into dressing 110.

In addition, because the dressing of the present invention, when assembled and applied to a patient, provides an essentially closed system (other than by permitting excess humidity to dissipate through the breathable cover), it is also possible for a dressing constructed in accordance with the present invention to be employed in negative pressure wound therapy. For example, rather than using syringe 115 in the embodiment of FIG. 10 to inject fluids into the dressing, by pulling the piston of an empty syringe, the syringe could be used to create a negative pressure environment in the wound environment. Alternatively, instead of the syringe 115, tube 114 instead may be connected to a conventional squeeze ball/valve arrangement or low-pressure vacuum pump to partially evacuate the dressing. In this manner, the patient or caregiver may periodically reduce the pressure within the compartment formed by dressing 110 to promote exudate flow, and speed the healing process.

With respect to FIG. 11, an alternative design of a dressing in accordance with the principles of the present invention is described. Dressing 120 includes support cushion 121, a wicking strip as described with respect to preceding embodiments (again omitted for clarity), reservoir 122 and cover 123. The support cushion, wicking strip, reservoir and cover are constructed substantially as described for preceding embodiments. Dressing 120 differs from preceding embodiments in that cover 123 includes bellows 124 that communicates with the vent that passes through the reservoir (see vent 44 in FIG. 1B). Bellows 124 preferably comprises a lightweight plastic or synthetic rubber and includes one-way valve 125, so that depressing bellows 124 induces a negative pressure within dressing 120. As for previously-described embodiments, cover 123 preferably comprises a breathable material that permits excess humidity to be released from within dressing, but is sufficiently air-tight to retain a negative pressure induced within the dressing by bellows 124 for an appropriate amount of time, e.g., 5-10 minutes, to stimulate exudate flow. In this manner, the patient or caregiver may periodically reduce the pressure within the compartment formed by dressing 120 by depressing bellows 124, thereby speeding the healing process with reduced or no pain or discomfort to the patient.

Referring now to FIGS. 12A and 12B, a further alternative embodiment of a wound dressing constructed in accordance with the principles of the present invention is described. As for the embodiment of FIG. 1, dressing 130 includes three discrete components that are assembled and applied over wound W on patient's epidermis E. In particular, dressing 130 includes support cushion 131, wicking strip 132, and reservoir 133, which may be pre-attached to cover 134. Preferably, components 131-134 are sized for use with one another and are enclosed in a sterile package with suitable instructions to enable the patient or caregiver to quickly and accurately apply the dressing.

Support cushion 131 preferably comprises a closed cell polyolefin foam and is designed to surround wound W and periwound region P, i.e., the region of epidermis E extending from the wound margin, to protect the wound and elevate reservoir 133 and cover 134 above the wound bed. In the embodiment of FIG. 12, support cushion 131 has a uniform height, so that reservoir 133 is supported directly by the upper surface of support cushion 131, as depicted in FIG. 12B. As for preceding embodiments, the lower surface of support cushion 131 includes a layer of biocompatible adhesive, which preferably is hydrophobic and breathable. Support cushion 131 preferably includes slits or perforations 135 that extend through the height of the support cushion to facilitate the escape of perspiration from beneath the support cushion when is it fastened to epidermis E. Support cushion 131 includes opening 136 that exposes a portion of the periwound region extending away from the margin of wound W, to permit placement of wicking strip 132, as depicted in FIG. 12B. As noted above, support cushion may comprise a breathable open weave spacer fabric instead of a closed cell polyolefin foam.

Wicking strip 132, which preferably comprises an open-cell polyurethane foam, overlays periwound region P between the margin of wound W and opening 136 of support cushion 131. In the embodiment of FIG. 12, wicking strip 132 is depicted as a curved strip of foam, although it may take other forms as described with respect to FIGS. 5 and 6. Wicking strip 132 preferably includes a layer of biocompatible adhesive, which preferably is hydrophobic and breathable, on its lower surface to adhere to the patient's epidermis. During application, wicking strip 132 fits within opening 136 of support cushion 131, so that the innermost edge of the wicking strip preferably overlaps the margin of the wound by 1-2 mm. For the embodiment of FIG. 12A, wicking strip 132 may be cut with a scissor to ensure that the foam is not overly compressed when adhered to the periwound region.

Still referring to FIG. 12, reservoir 133 preferably comprises a sandwich of different density open cell polyurethane foams, as described with respect to the embodiment of FIG. 1, and comprises one or more foams selected to absorb exudate from wicking strip 132 and to sequester the exudate away from the wound bed. Reservoir 133 may be fastened to the underside of cover 134, and may include a layer of adhesive along the perimeter of its lower surface to adhere to the upper surface of support cushion 131. Reservoir 133 includes a hydrophobic gasket 137 disposed on its lateral face, as depicted in FIG. 12B, so that exudate drawn into the reservoir from wicking strip 132 cannot seep out of the lateral face of the reservoir. Gasket 137 may comprise a hydrophobic film applied to the exterior lateral surface of reservoir 133. Alternatively, gasket 137 may comprise a closed cell hydrophobic foam adhered to the perimeter of reservoir 132, which is capable of supporting a compressive load (like the material of support cushion 131). Reservoir 133 is sized so that its outer edges are supported on the upper surface of the innermost portions of support cushion 131 and wicking strip 132. Reservoir 133 preferably includes one or more vents 138 that assist in modulating the humidity within the dressing through cover 134.

Cover 134 is preferably a breathable material and overlays reservoir 133, and includes a layer of adhesive along the circumference of its lower surface that may be used to removably secure reservoir 133 in engagement with epidermis E and to adhere cover 133 to epidermis E. In accordance with one aspect of the present invention, cover 134 includes plurality of holes 139 that permit the reservoir and cover to be correctly aligned with the wicking strip and support cushion during application. In particular, holes 139 permit the caregiver to sight through the holes during application of the cover and reservoir to confirm proper positioning of the cover and reservoir relative to support cushion 131.

As illustrated in FIG. 12B (from which cover 134 has been omitted for clarity), during use of dressing 130, exudate EX flows out of wound W at a flow rate that depends on many factors, including the pressure with which wicking strip 132 is pressed against the periwound region, the lateral profile of the wicking strip as described above with reference to FIGS. 5A-5C, the characteristics of wound W, and the consistency of the exudate. As exudate EX is released from the wound, it contacts and is absorbed by wicking strip 132. Wicking strip 132 transports exudate EX laterally (in the plane of epidermis E) and then vertically (perpendicular to the plane of epidermis E) to reservoir 133. Exudate transported laterally may eventually reach support cushion 131, which is formed of a hydrophobic material, and inhibits further lateral transport of the exudate. Instead, exudate EX is transported vertically from wicking strip 132 and into reservoir 133, which sequesters exudate away from the wound. Reservoir 133 preferably has a large absorptive surface area and the capacity to hold large amounts of exudate, e.g., sufficient capacity so that reservoir 133 need only be replaced once every few days. Additionally, gasket 137 inhibits leakage of exudate onto periwound region P. Because Reservoir 133 is constructed of a breathable material, the water in the exudate absorbed by reservoir 133 is released in the form of vapor V into the atmosphere via breathable cover 134.

Referring now to FIGS. 13A and 13B, an alternative embodiment of a reservoir and cover suitable for use with the dressing of the present invention is described. In the embodiment of FIG. 1, sidewall 21 provides structural support for the reservoir against compressive loads applied to the dressing, while gasket 137 of reservoir 133 provides a similar function in the embodiment of FIG. 12. As described earlier, however, it may be desirable, with an irregularly shaped wound, to custom-fit a support cushion using a strip. A problem with this approach, however, is that if the reservoir is cut to the overall shape of the wicking strip and support cushion, the gasket or hydrophobic film at the edge of the reservoir may be removed, and exudate may leak from the exposed edge of the reservoir. One solution is to drape the cover over the sides of the cut reservoir, having this approach does not provide mechanical support to reservoir to resist compressive loads.

One solution to the foregoing concern is construction for the reservoir and cover depicted in FIGS. 13A and 13B. In this embodiment, cover 140 includes rigid inverted basket 141 joined along its lower edge to elastomeric adhesive bandage 142. Reservoir 150, which may be similar in construction to reservoir 133 of FIG. 12, and includes gasket 137, is disposed within basket 141. Basket 141 is formed from plurality of radial struts 143, circumferential struts 144 and vertical struts 145. Struts 143, 144 and 145 preferably are formed from a tough, resilient plastic, such as polyurethane, and protect reservoir 150 from compressive loads.

Advantageously, cover 140 and reservoir 150 are preformed in specific sizes, e.g., small, medium and large diameters. During application of the inventive dressing to an irregularly shaped wound, the wicking strip and support cushion may be custom-fit from strip-shaped support cushion and wicking strips by wrapping the support cushion and wicking strip around the wound. A suitably sized cover 140 and reservoir 150 may then be selected from the preformed sizes such, when applied, that the outer edge of the reservoir sits atop at least the innermost rings (or spirals) of the support cushion. For example, if the wound is relatively small, the reservoir may extend to the outermost ring of the support cushion. On the other hand, if the wound is large, the reservoir may sit atop the innermost ring of the support cushion. Since for this embodiment it is not necessary to cut the outer edge of the reservoir, the gasket remains intact and prevents diffusion of exudate through the lateral edges of the reservoir. In addition, the basket provides mechanical support and protection for the reservoir against compressive loads, thus preventing exudate absorbed into the reservoir from being inadvertently released into the wound bed.

Kits

The components of a dressing constructed in accordance with the principles of the present invention, illustratively dressing 10 of FIG. 1, may be provided to patients or caregivers as a kit 160, illustrated in FIG. 14. Kit 160 includes a cardboard or other sturdy, disposable backing 161 upon which support cushion 20, wicking strip 30, reservoir 40, and cover 50 are removably mounted. Examples of alternative disposables backing 161 are dark, colored or translucent trays of materials such as polystyrenes (for example available from Sealed Air Corp., Elmwood Park, N.J., USA; or Perfecseal®, a BEMIS Co., Oshkosh, Wis., USA). Kit 160 may also include additional components, e.g., extra wicking strips 30, or different sizes and shapes of support cushion 20, to be able to accommodate different sizes and shapes of wounds. In an alternative embodiment, the components of dressing 10 are instead provided in one or more compartments of a tray.

In the illustrated embodiment, foldable tabs 162 cut from backing 161 and/or pieces of excess material adhered to backing 161 may be used to secure the components of dressing 10 to backing 161 until they are needed. For example, the hole in support cushion 20 may be formed by cutting piece 163 from a layer of flange material, and then adhering that piece 163 to backing 161. Because piece 163 snugly fits into the hole of support cushion 20, the friction between piece 163 and support cushion 20 serves to removably retain support cushion 20 on backing 161 without the need for additional adhesive or tabs, until removed by the patient or caregiver. Similarly, reservoir 40 may be cut from the center of a larger piece 164 that is subsequently adhered to backing 161. Friction between reservoir 40 and piece 164 retains reservoir 40 frictionally engaged on backing 161 without the need for additional adhesive or tabs, until removed for use. Alternatively, tabs 162 may be used to secure all of the components onto backing 161.

Instructions for use 165 for applying the different components of dressing 10 to a patient may be printed on backing 161, e.g., instructions for implementing the method described with respect to FIG. 3. The instructions may be sterilized so that they may be safely used in a sterilized field, such as an operating room. The adhesive layers on the different components are covered with non-stick, removable liners that may be color coded to guide the patient or caregiver in determining the order in which to apply the components of dressing 10. Such non-stick liners may facilitate handling of the different components of dressing 10, e.g., while placing support cushion 20 on the patient's epidermis.

Kit 160 preferably further includes a pouch (not shown) in which backing 161 and dressing 10 are sealed until needed. Preferably, the pouch is transparent on at least its upper surface, allowing backing 161 and the other components to be viewed. Additionally, instructions for use 165 may be located on backing 161 so as to make possible reading of the instructions before opening the pouch. The pouch also may be constructed to aid retention of the components of dressing 10 on backing 161. Kit 160 preferably is sterilizable, e.g., may be sterilized after assembly, such that the contents of the pouch remain sterile until it is opened, e.g., immediately before the dressing is applied to a patient. The pouch preferably comprises a material that retains its integrity during conventional sterilizing procedures, e.g., exposure to gamma radiation, to an electron beam, or to ethylene oxide gas.

It is envisioned that a typical wound care treatment environment, such as a hospital, wound care outpatient clinic or doctor's office, may stock an inventory of kits 160 designed for use with different sizes or shapes of wounds. For example, a plurality of kits 160 may be manufactured having support cushion 20, wicking strip 30, reservoir 40, and cover 50 in a variety of sizes and shapes, according to different wound sizes and shapes with which they may be suitable for use. Alternatively, or in addition, individual components of the dressing, such as the wicking strips and reservoirs, may be individually packaged, for example to permit periodic replacement of the wicking strip or reservoir with greater frequency than the dressing as a whole. As a still further alternative, as described above, the wicking strip and support cushion may be individually packaged in a roll form, so that the dressing may be applied in a custom-fit manner, while cover and reservoir combinations, such as described above with respect to FIG. 13, may be made available in discrete sizes, so that the dressing may be applied to a wide range of wound topologies.

INCORPORATED REFERENCES

The following commonly-owned patent publications describe additional materials and structures that may be used in various embodiments of the invention, and are each incorporated by reference herein in their entireties:
U.S. Patent Publication No. 2006/0235347;
U.S. Patent Publication No. 2007/0142757;
U.S. Patent Publication No. 2007/0142761;
U.S. Patent Publication No. 2007/0161937;
U.S. Patent Publication No. 2007/0161938; and
U.S. Patent Publication No. 2007/0191754.

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A dressing for protecting a wound and managing exudate released from the wound, the wound having a margin and being surrounded by a periwound region, the dressing comprising:
   a support cushion configured to surround the wound and the periwound region;
   a wicking strip configured to be positioned immediately adjacent the margin of the wound in the periwound region between the support cushion and the margin of the wound and independently of the support cushion such that the wicking strip wicks the exudate from the margin of the wound and substantially inhibits contact between the exudate and the periwound region; and
   a reservoir configured to be suspended over and in engagement with the wicking strip so that the wicking strip transfers exudate from the wound to the reservoir; and
   a cover configured to be positioned over the reservoir.

2. The dressing of claim 1, wherein the cover is configured to retain the reservoir in engagement with the wicking strip.

3. The dressing of claim 1, wherein the support cushion further comprises a sidewall and a flange, the flange defining a ledge to accept a portion of the reservoir.

4. The dressing of claim 3, wherein the support cushion comprises a hydrophobic material, the wicking strip and the reservoir comprise hydrophilic materials, and the sidewall, ledge and flange inhibit seepage of exudate out of the reservoir and wicking strip onto the periwound region.

5. The dressing of claim 1, wherein a plurality of slits are disposed in the support cushion.

6. The dressing of claim 1, wherein the wicking strip has a length and a height, and the height varies along the length such that engagement of the reservoir to the wicking strip induces a pressure gradient in the periwound region.

7. The dressing of claim 1, wherein the reservoir comprises a first hydrophilic layer, a non-stretchable mesh or scrim, and a second hydrophilic layer.

8. The dressing of claim 1, wherein the cover comprises a breathable material.

9. The dressing of claim 8, wherein a vent is defined in the reservoir, the vent permitting humidity over the wound to escape.

10. The dressing of claim 1, wherein the support cushion further comprises a tube that enables fluids to be injected into the dressing without removing the reservoir or cover.

11. The dressing of claim 1, wherein the cover further comprises a bellows configured to be depressed to periodically induce a negative pressure within the dressing.

12. A method for protecting a wound and managing exudate released from the wound, the wound having a margin surrounded by a periwound region, the method comprising:
   surrounding the wound and the periwound region with a support cushion;
   applying a wicking strip immediately adjacent the margin of the wound in the periwound region between the support cushion and the margin of the wound and independently of the support cushion such that the wicking strip wicks the exudate from the margin of the wound and substantially inhibits contact between the exudate and the periwound region; and
   applying a reservoir over the wicking strip,
   wherein the wicking strip transfers exudate from the wound to the reservoir.

13. The method of claim 12, further comprising substantially filling the periwound region between the support cushion and the margin of the wound with the wicking strip.

14. The method of claim 12, wherein the support cushion includes a stepped profile that defines a ledge and a recess, the method further comprising fitting the reservoir within the recess so that the reservoir engages the ledge and is suspended over the wound.

15. The method of claim 14, wherein the support cushion comprises a hydrophobic material and the wicking strip and the reservoir comprise hydrophilic materials, the method further comprising inhibiting lateral flow of exudate out of the reservoir or the wicking strip onto the periwound region.

16. The method of claim 15, wherein urging the reservoir into engagement with the wicking strip further comprises applying a compression wrap over the dressing.

17. The method of claim 12, further complying stimulating exudate flow by urging the reservoir into engagement with the wicking strip to induce pressure in the periwound region.

18. The method of claim 17, wherein the wicking strip has a length and a height and the height varies along the length, and wherein the method further comprises applying the wicking strip in the periwound region to induce a pressure gradient in the periwound region when the reservoir is engaged to the wicking strip.

19. The method of claim 12, further comprising applying a medication to the wound before applying the reservoir.

20. A kit for a dressing for use in protecting a wound and managing exudate released from the wound, the wound having a margin surrounded by a periwound region, the kit comprising:
   a support cushion configured to surround the wound and the periwound region;
   a wicking strip configured for application immediately adjacent the margin of the wound in the periwound region between the support cushion and the margin of the wound and independently of the support cushion such that the wicking strip wicks the exudate from the margin of the wound and substantially inhibits contact between the exudate and the periwound region;
   a reservoir configured to be applied over the wicking strip;
   a backing upon which the support cushion, wicking strip, and reservoir are mounted; and
   instructions for use printed on the backing, the instructions for use describing steps for assembling the dressing.

\* \* \* \* \*